(12) United States Patent
Becker et al.

(10) Patent No.: US 6,303,117 B1
(45) Date of Patent: Oct. 16, 2001

(54) **ICE GRANULES CONTAINING ENDOTOXINS OF *BACILLUS THURINGIENSIS* ISRAELENSIS (BTI) OR *BACILLUS SPHAERICUS* (BS)**

(76) Inventors: Norbert Becker, Bauhausstrasse 46, D-67069 Ludwigshafen; Peter Mercatoris, Obere Riedstrasse 21, D-68309 Mannheim, both of (DE)

( * ) Notice: Subject to any disclaimer, the term of this patent is extended or adjusted under 35 U.S.C. 154(b) by 0 days.

(21) Appl. No.: 09/331,571

(22) PCT Filed: Oct. 17, 1997

(86) PCT No.: PCT/EP97/05747
§ 371 Date: Jun. 28, 1999
§ 102(e) Date: Jun. 28, 1999

(87) PCT Pub. No.: WO98/28984
PCT Pub. Date: Jul. 9, 1998

(30) Foreign Application Priority Data

Dec. 28, 1996 (DE) .............................................. 196 54 652

(51) Int. Cl.$^7$ ...................................................... A01N 63/00
(52) U.S. Cl. .................................. 424/93.461; 424/93.46; 424/424; 424/489; 514/2; 530/350
(58) Field of Search ........................... 424/93.461, 93.46, 424/489; 514/2; 530/350

(56) References Cited

U.S. PATENT DOCUMENTS

| | | | |
|---|---|---|---|
| 4,166,112 | 8/1979 | Goldberg | 424/93 |
| 4,276,381 | 6/1981 | Sakimae et al. | 435/179 |
| 4,902,507 | * 2/1990 | Morris et al. | |

FOREIGN PATENT DOCUMENTS 41 33 889   4/1993   (DE) .

* cited by examiner

*Primary Examiner*—Leon B. Lankford, Jr.
(74) *Attorney, Agent, or Firm*—Foley & Lardner

(57) ABSTRACT

Endotoxins, in a preparation of ice granules, from *Bacillus thuringiensis* and/or *Bacillus sphaericus* are used to combat mosquito larva.

16 Claims, No Drawings

ICE GRANULES CONTAINING ENDOTOXINS OF *BACILLUS THURINGEINSIS* ISRAELENSIS (BTI) OR *BACILLUS SPHAERICUS* (BS)

The subject of the present invention are new ice granules produced from aqueous suspensions of *Bacillus thuringiensis israelensis* (BTI) or *Bacillus sphaericus* (BS) endotoxins which are used in the combatting of gnat larvae.

Gnats are dangerous transmitters of diseases, e.g. malaria, bleeding fever (dengue, DHF), encephalitis or lymphatic filiaroses. However, in the European region, above all things in the case of massive occurrence, they are a considerable plague which significantly diminishes the quality of life. Worldwide, extensive measures are made for the combatting of gnats and more than 50,000 tonnes of chemical insecticides are thereby used anually. However, besides the objective use in the reduction of gnat frequency, these chemicals cause considerable toxicological risks since they not only damage the gnats or their larvae but are also active against other organisms. Ecological risks are thereby also given since the simultaneous damaging of other insects, for example of the non-biting midges, disturbs the food chain for fish and birds. Therefore, one has sought alternatives which act more selectively against gnats or their larvae.

Besides the chemical insecticides, for many years bacterial insecticides have been the subject of intensive research work.

In 1977, Goldberg and Margalit isolated from a sample originating from gnat breeding places in the Negev desert a *Bacillus thuringiensis* strain which proved to be pathogenic towards larvae of various midges, especially mosquitoes and gnats. Today, this is classified as *Bacillus thuringiensis* var. *israelensis* and also designated as pathotype B for the differentiation from a *Bacillus thuringiensis* pathotype A which is active against *lepidoptera*. In U.S. Pat. No. 4,166,112, the use of BTI as insecticide is claimed.

Microbiological preparations based on *Bacillus thuringiensis* H-14 and Bacillus sphaericus have, in preceding years, proved to be effective in the battle against gnats. They act very selectively and kill off only the larvae of few kinds of midges, especially gnats. For other animals and humans, even close relatives of gnats, these agents are, according to present day knowledge, not dangerous. The effectiveness thereby depends upon protein crystals (endotoxins) which the bacillae produce at the end of their growth period simultaneously with the spore formation. When these endotoxins are taken up by the gnat larvae together with the feed, they are activated in the gut of the midge to give the toxin, deposit on the middle gut cells and cause these to burst by osmo-regulatory effects. Thus, the midge larvae die within a few minutes to hours.

Necessary prerequisites of the effectiveness of endotoxins are a) a sufficiently high concentration in which they are taken up by the gnat larvae, b) the activation to the toxin in the alkaline gut medium of the midge larvae by corresponding proteases, and c) the presence of corresponding receptor sites on the gut cells of the midges to which these toxins bind.

That these endotoxins act so specifically appears to be due to the fact that, above all, the receptor sites are not present in the case of other animals or the proteolytic breakdown takes place in another way.

Since these microbiological feed poisons can only be used against the mosquito, gnat and midge larvae and, on the other hand, as proteins, are broken down relatively quickly by the most different micro-organisms occurring in nature, it is necessary to introduce the preparations in suitable concentration into the breeding waters after the larvae have hatched.

Hitherto, the product was mixed as powder formulation or liquid concentrate with appropriate amounts of water and sprayed as suspension over the infested waters. These forms of preparation have the great disadvantage that, in the case of distribution from the air, they deposit on branches or leaves projecting over the waters and thus do not get to the effective place. In unfavourable areas, for example primaeval forests, a loss of up to 80% can result.

Furthermore, it is known to work up the endotoxins, together with sand or maize bran, to give granulates which can then be sprinkled in solid form. Furthermore, from DE-41 33 889-C2 are known forms of composition, i.e. tablets, which, in the presence of water, evolve gas which takes care of the spreading out of the active material. In the case of application from the air, these solid compositions admittedly trickle through the branches and thus get to the effective place but are comparatively expensive and, due to the adjuvants contained in large amount, contaminate the waters.

Therefore, the task arises to find a form of composition which permits the preparations to be used in solid form without undesired adjuvants being used.

Surprisingly, this task is solved by the features characterised in the main claim and promoted by the features according to the subsidiary claims.

It is surprising that ice granules which are produced by freezing of appropriate aqueous endotoxin suspensions, which possibly also contain adjuvants in small amount, cause no damage to the endotoxins contained but rather a microbial breakdown is slowed down in the case of normal storage at −10 to −20° C.

The ice granules according to the invention are so adjusted in their composition that they are somewhat lighter than water (D=0.95 to 0.98) whereby, in the case of introduction into the water, they float on the surface. Due to slow thawing, the endotoxin is then liberated on the surface of the granulate which slowly sinks whereby the BTI crystals distribute uniformly in the whole of the body of water.

For the composition of the ice granules, a high portion of BTI is desired in order to transport as small a weight as possible in the supplying aircraft. On the other hand, the content is to be so small that a uniform distribution over the surface to be impinged is ensured.

It has proved to be worthwhile to apply about 250 g ($2.5 \cdot 10^9$ ITU=international toxic units) of endotoxin to 1 ha water and to use therewith 5–50 l of water as dilution agent which leads to a 100% mortality in the case of mosquitoes of the genus Aedes and Culex.

For the production of the ice granules, the commercially available BTI and *Bacillus sphaericus* liquid concentrates are mixed homogeneously with water so that an end concentration of 1–200 g, preferably 5–100 g of endotoxin per l of water results. In the case of use of solid endotoxin powders, an addition of wetting agents, suspension adjuvants and/or thickeners is useful in order to ensure a uniform mixing. The granulate with a grain diameter of 2–20 mm, preferably of 3–5 mm, is produced either directly from the mixture with an ice machine or first a fluffy ice is produced with a "snow cannon" and further pressed in a pelleting machine to give granules. Grinding of comparatively large ice blocks and sieving out of a fine granulate is also possible but not preferred since the bodies thereby resulting have an irregular shape and thus, under pressure, easily grow together again. Commercially available machines with appropriate cooling devices can be used. The ice granulate is packed into thermo-sacks and then stored at −20° C. in a cold-storage depot. Appropriately cooled containers in the transport vehicles and in the supplying aircraft here also permit comparatively long transport times. The application itself takes place via conventional gyro- or simplex sprinklers. Sprinkling breadths of about 20 meters could be achieved.

A great advantage of the ice granulate lies, above all, therein that no losses of active material (BTI and *Bacillus sphaericus*) are to be observed. In the case of the application of BTI-sand granulate, about 20–30% of the active material are lost by the rubbing off in the case of application. The BTI/*Bacillus sphaericus* powder-oil mixture is removed from the sand grains as carrier materials when it is catapulted with pressure from the scattering device. One does not have this loss in the case of the application of the ice granulate since the active material is bound in the granulate.

A further advantage results from the physical properties of ice. With a specific weight of 0.96 g/cm$^3$, ice is lighter than water and floats on the water surface. In the case of dissolving, the granulate liberates the active material which thus remains sufficiently long on the water surface in the zone in which the gnats frequently take up their nutrition. Comparatively small amounts of toxin thereby already suffice in order to kill off the gnat larvae.

Experiences have shown that, in the case of the application of BTI-oil-sand granulate, about 25 kg of granulate per hectare must be applied. In order to achieve a sufficient action, the granulate must contain about 900 g of BTI powder with an activity of about 10,000 ITU/mg. In the case of costs of about 140.00 DM per kg of concentrate, there arise material costs of more than 130.00 DM per hectare of breeding area. On the other hand, one litre of liquid concentrate only costs about 15.00 DM so that the material costs run to only 30.00 DM in addition to production and storage costs. In all, the material costs per hectare are, in the case of the use of the new granulate formulation, about 60.00 DM and thus amount to less than half in comparison with the costs in the case of conventional granulates.

A further embodimental form of the ice granulate according to the invention is especially suitable for the specific combatting of midge larvae living on the bottom of the water, such as for example midge larvae which belong to the family Chironomini, e.g. *Chironomus plumosus* or *Chironomus thummi*. The combatting of these non-biting midges can be necessary when their population gets out of hand. For example, in the case of foodstuffs, due to the enormous number of the bugs, dangers arise from a hygienic point of view. The swarms can thus also lead to such strong impairment of the vision that air traffic is endangered. Furthermore, the midges can transmit allergies.

Whereas the gnat larvae preponderantly take their nutrition in the upper water layers by filtration, the larvae of the midges populate preponderantly the sediment of permanent waters, e.g. of rivers, stagnant water or overloaded settling pools. The larvae there build thread or gelatinous tubes. The housings mostly represent tubes open at both ends embedded in sludge or sand. The greater part of the midge larvae belong to the detritus and micro-organism eaters. In their living tubes, the larvae produce a water current and, in this way, filter from the water precipitated materials in the form of dying or dead organisms. Parts of the gelatinous funnel are eaten by the larvae with the swirled in suspended particles.

Thus, the endotoxins of BTI must be so given that, on the one hand, they sink to the bottom of the water and, on the other hand, no active materials are lost in the sinking. This is achieved by an ice granulate formulation according to the invention which has a specific weight of >1, thus is heavier than water and sinks to the bottom of the water. The physical properties necessary for the sinking are achieved by addition of ballast materials to tie granulate. For this purpose, mineral carriers, such as grit or sand, can be used.

It has proved to be especially advantageous to place a protective envelope in the form of ice around the granulate. Active material losses are hereby avoided since a dissolving off of the active material during the sinking is prevented. If the BTI-ice-mineral granulate has sunk to the bottom of the water, the BTI-ice envelope separates from the mineral carrier and can be taken up by the larvae with the feed.

The production of the BTI-ice-mineral granulate can take place, for example, in a conventional cement mixer or similar devices. Suitable particles of the chosen carrier material, e.g. grit particles, with grain sizes in the region of about 5 mm are introduced into the mixer and cooled with liquid nitrogen or in other known way to about −10° C. Thereafter, with running machine, one sprays it uniformly with an aqueous BTI suspension, whereby a BTI-ice mantle forms around the carrier. This is repeated up to the achievement of the desired granulate size or active material concentration. The active material content of the BTI-ice envelope can be varied according to the type of midge or larvae stage. Preferably, one also places around the so obtained biphasic granulate grains a protective layer of pure ice in that one finally sprays these with pure water. The added amount of water thereby depends on the sinking depth and water temperature. Furthermore, it is possible to introduce biologically decomposable coloured materials into the individual layers in order to make visible the covering thicknesses and to observe the dissolving off of the envelopes.

A preferred dosaging for the BTI-ice-mineral granulate lies in the region of about 70 kg/ha of water surface which corresponds approximately to 15 l of a BTI concentrate with an activity of 1200 ITU/mg. The granulate grains sink within a few seconds to the bottom of the water and there give off their active material. In outdoor experiments on the Danube, larval populations of *Chironomus plumosus* could be significantly reduced.

The granulate can be applied from the ground or better also with a helicopter with thermo-insulated rotary scatterer.

The use of the new granulate formulations is recommended especially in large surface breeding areas with dense plant growth.

EXAMPLE 1

2 l BTI concentrate (Vectobac 12 AS—mark of Abbott Lab., USA) with an activity of $1.2 \cdot 10^3$ ITU/mg are suspended in 30 l water and worked up by means of a hail ice machine to approximately spheroidal granulates or pellets with a diameter of 5 mm or volume of 0.125 ml. The amount is applied with a rotary scatterer in an aircraft over the breeding ground (about 1 ha) so that about $2.4 \cdot 10^9$ ITU/ha of endotoxin are applied. Per square metre of breeding ground, this gives about 24 grains which suffices for a uniform distribution of the active material. The amount applied leads in the experimental area to a 100% mortality of the mosquito larvae of the genus Culex and Aedes.

EXAMPLE 2

30 kg of grit particles with a grain size of about 5 mm are introduced into a cement mixer and cooled with liquid nitrogen to below −10° C. Thereafter, BTI concentrate is sprayed on uniformly with the machine running. This procedure is repeated several times until the ice mantel formed around the mineral nucleus is sufficiently large. In all, 15 l of BTI concentrate are applied. Subsequently, about 10 l of water are sprayed on the granulate as protective envelope. The granulate is applied with a helicopter in a dosing of 70 kg/ha. Larvae populations of *Chironomus plumosus* on the Danube were thereby significantly reduced.

What is claimed is:

1. A composition for the combatting gnat larvae that is in ice granulate form and has the following weight ratio: 1–200 g *Bacillus thuringiensis* israelensis and/or *Bacillus sphaericus* endotoxin to each 1 kg of water.

2. A composition according to claim 1, further comprising from 10 to 100 g/l of adjuvants and/or other active materials.

3. A composition according to claim 1, wherein the granules have a diameter of 2–20 mm.

4. A composition according to claim 1, wherein the ice granulate is associated with a mineral carrier, thereby forming a biphasic granulate, and has a specific weight of >1 g/cm$^3$.

5. A composition according to claim 4, wherein said mineral carrier is grit or sand.

6. A composition according to claim 5, wherein a protective envelope of ice surrounds the biphasic granulate.

7. A composition according to claim 3, wherein the granules have a diameter of 3–5 mm.

8. A composition according to claim 7, wherein each granule has a weight of 0.01–1.0 g.

9. A method of combatting gnat larvae, comprising applying to water infested with gnat larvae from 0.1–100 ppm of ice granules having the following weight ratio: 1–200 g *Bacillus thuringiensis* israelensis and/or *Bacillus sphaericus* endotoxin to each 1 kg of water.

10. A method according to claim 9, wherein said composition further comprises from 10 to 100 g/l of adjuvants and/or other active materials.

11. A method according to claim 10, wherein the granules have a diameter of 2–20 mm.

12. A method according to claim 9, wherein the ice granulate is associated with a mineral carrier, thereby forming a biphasic granulate and has a specific weight of >1 g/cm$^3$.

13. A method according to claim 12, wherein said mineral carrier is grit or sand.

14. A method according to claim 13, wherein a protective envelope of ice surrounds the biphasic granulate.

15. A method according to claim 11, wherein the granules have a diameter of 3–5 mm.

16. A method according to claim 9, wherein each granule has a weight of 0.01–1.0 g.

* * * * *